(12) United States Patent
Li

(10) Patent No.: US 6,524,572 B1
(45) Date of Patent: Feb. 25, 2003

(54) TARGETING RECOMBINANT VIRUS WITH A BISPECIFIC FUSION PROTEIN LIGAND IN COUPLING WITH AN ANTIBODY TO CELLS FOR GENE THERAPY

(75) Inventor: Yibing Li, San Francisco, CA (US)

(73) Assignee: Rainbow Therapeutic Company, San Francisco, CA (US)

( * ) Notice: Subject to any disclaimer, the term of this patent is extended or adjusted under 35 U.S.C. 154(b) by 0 days.

(21) Appl. No.: 09/604,107

(22) Filed: Jun. 26, 2000

(51) Int. Cl.[7] .................. A61K 98/00; C12N 15/86; C12N 15/861; C07K 16/46; C07K 16/18
(52) U.S. Cl. .................. 424/93.2; 424/93.1; 424/93.6; 435/69.1; 435/69.7; 435/235.1; 435/320.1; 435/455; 435/456; 435/325; 435/366; 530/350; 530/387.1; 530/387.3; 530/388.22
(58) Field of Search .................. 435/235.1, 69.1, 435/320.1, 69.7, 455, 456, 325, 366; 424/93.1, 93.2, 93.6; 530/350, 387.1, 387.3, 388.22

(56) References Cited

U.S. PATENT DOCUMENTS

| 5,422,427 A | * | 6/1995 | Russell et al. | |
|---|---|---|---|---|
| 5,770,442 A | * | 6/1998 | Wickham et al. | |
| 5,834,589 A | * | 11/1998 | Meruelo et al. | 530/350 |
| 5,871,727 A | * | 2/1999 | Curiel | |
| 6,057,155 A | * | 5/2000 | Wickham et al. | |
| 6,060,316 A | * | 5/2000 | Young et al. | |

FOREIGN PATENT DOCUMENTS

| WO | WO 98/11221 | * | 3/1998 |
|---|---|---|---|

* cited by examiner

*Primary Examiner*—David Guzo

(57) ABSTRACT

Use of recombinant viral vector for gene therapy is hampered by the native virus-host interaction. Non-specific gene transfection causes adverse effects in gene therapy. To solve this problem, a fusion protein ligand capable of modifying viral tropism has been created. The fusion protein comprises a viral cellular receptor at one end and an antibody Fc-binding protein at the other end. By the design, the fusion protein ligand when coupled with an antibody can block the native viral infection and redirect the virus to specific cellular surface marker as long as the antibody binds to this marker. Using adenovirus and adenoviral receptor as an example, the fusion protein ligand when coupled with anti ICAM-1 IgG redirects virus to cultured human endothelial cells expressing ICAM-1. Infection by viruses depends on the presence of viral receptor on the host cells and this requirement limits the use of viral vector for gene therapy. The current invention circumvents this requirement, broadens the spectrum of diseases amenable to gene therapy using viral vectors, enhances the viral transfection efficiency in cells or tissues that are refractory to these viruses, and finally provides a safer and more flexible system for gene targeting.

12 Claims, 11 Drawing Sheets

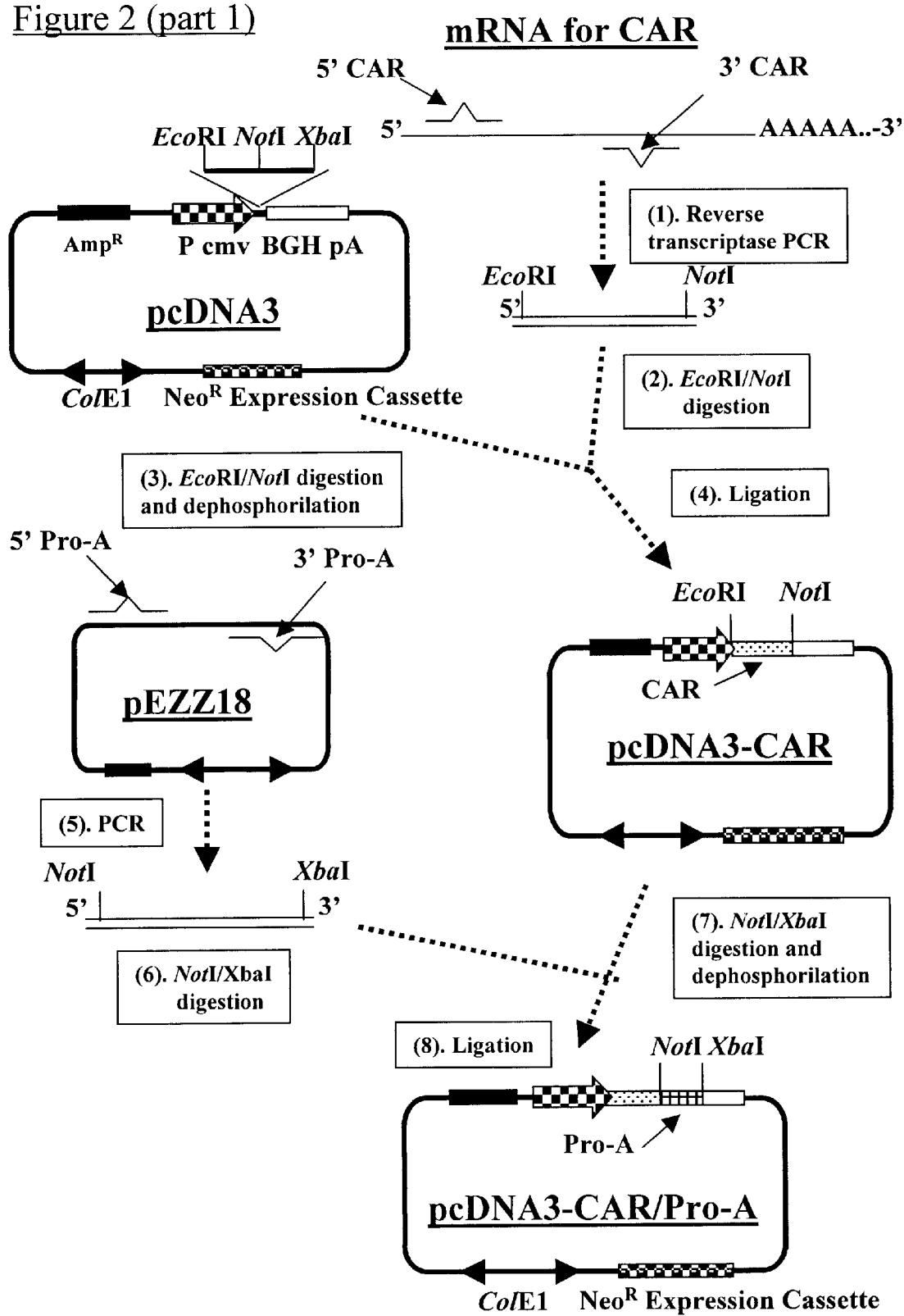
Figure 2 (part 1)

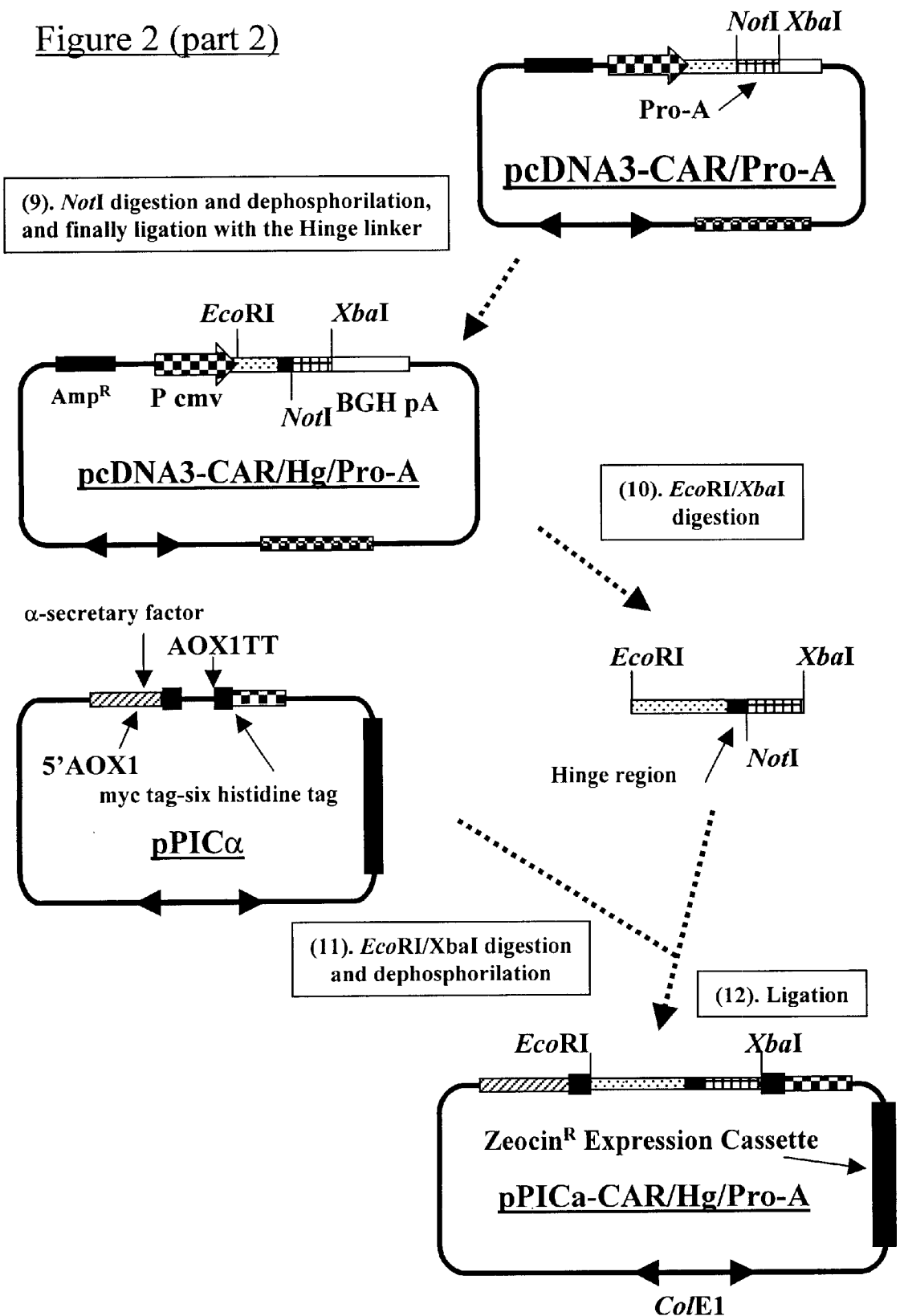
Figure 2 (part 2)

Figure 3B

```
Met Arg Phe Pro Ser Ile Phe Thr Ala Val Leu Phe Ala Ala
Ser Ser Ala Leu Ala Ala Pro Val Asn Thr Thr Thr Glu Asp
Glu Thr Ala Gln Ile Pro Ala Glu Ala Val Ile Gly Tyr Ser
Asp Leu Glu Gly Asp Phe Asp Val Ala Val Leu Pro Phe Ser
Asn Ser Thr Asn Asn Gly Leu Leu Phe Ile Asn Thr Thr Ile
Ala Ser Ile Ala Ala Lys Glu Glu Gly Val Ser Leu Glu Lys
Arg Glu Ala Glu Ala Glu Phe Ala Arg Ser Leu Ser Ile Thr
Thr Pro Glu Glu Met Ile Glu Lys Ala Lys Gly Glu Thr Ala
Tyr Leu Pro Cys Lys Phe Thr Leu Ser Pro Glu Asp Gln Gly
Pro Leu Asp Ile Glu Trp Leu Ile Ser Pro Ala Asp Asn Gln
Lys Val Asp Gln Val Ile Ile Leu Tyr Ser Gly Asp Lys Ile
Tyr Asp Asp Tyr Tyr Pro Asp Leu Lys Gly Arg Val His Phe
Thr Ser Asn Asp Leu Lys Ser Gly Asp Ala Ser Ile Asn Val
Thr Asn Leu Gln Leu Ser Asp Ile Gly Thr Tyr Gln Cys Lys
Val Lys Lys Ala Pro Gly Val Ala Asn Lys Lys Ile His Leu
Val Val Leu Val Lys Pro Ser Gly Ala Arg Cys Tyr Val Asp
Gly Ser Glu Glu Ile Gly Ser Asp Phe Lys Ile Lys Cys Glu
Pro Lys Glu Gly Ser Leu Pro Leu Gln Tyr Glu Trp Gln Lys
Leu Ser Asp Ser Gln Lys Met Pro Thr Ser Trp Leu Ala Glu
Met Thr Ser Ser Val Ile Ser Val Lys Asn Ala Ser Ser Glu
Tyr Ser Gly Thr Tyr Ser Cys Thr Val Arg Asn Arg Val Gly
Ser Asp Gln Cys Leu Leu Arg Leu Asn Val Val Pro Pro Ser
Asn Lys Ala Gly Leu Ile Ala Ala Pro Lys Pro Ser Thr Pro
Pro Gly Ser Ser Ala Ala Ala Asp Asn Lys Phe Asn Lys Glu
Gln Gln Asn Ala Phe Tyr Glu Ile Leu His Leu Pro Asn Leu
Asn Glu Glu Gln Arg Asn Ala Phe Ile Gln Ser Leu Lys Asp
Asp Pro Ser Gln Ser Ala Asn Leu Leu Ala Glu Ala Lys Lys
Leu Asn Asp Ala Gln Ala Pro Lys Val Asp Asn Lys Phe Asn
Lys Glu Gln Gln Asn Ala Phe Tyr Glu Ile Leu His Leu Pro
Asn Leu Asn Glu Glu Gln Arg Asn Ala Phe Ile Gln Ser Leu
Lys Asp Asp Pro Ser Gln Ser Ala Asn Leu Leu Ala Glu Ala
Lys Lys Leu Asn Asp Ala Gln Ala Pro Asn Leu Glu Gln Lys
Leu Ile Ser Glu Glu Asp Leu Asn Ser Ala Val Asp His His
His His His His
```

**p < 0.01

TARGETING RECOMBINANT VIRUS WITH A BISPECIFIC FUSION PROTEIN LIGAND IN COUPLING WITH AN ANTIBODY TO CELLS FOR GENE THERAPY

BACKGROUND OF THE INVENTION

1. Field of the Invention

The current invention relates to the use of a fusion protein ligand to couple with an antibody species to target recombinant viruses to specific cell or tissue of interest. The current invention can be used in viral vector based gene therapy. In the use for gene therapy, current invention broadens the spectrum of diseases amenable to gene therapy using viral vectors, enhances the viral transfection efficiency in cells or tissues that are refractory to the viruses, and finally provides a safer and more flexible system for gene targeting. Current invention can also be used in experimental setting to selectively transfect specific cells or tissues of interest in a mixed cell or tissue environment.

2. Description of Prior Art

Infectious microorganism, especially those by virus, is characteristically tissue and/or species specific. This characteristic is named viral tropism. It has been known that the tropism is mainly associated with the fact that viral entry requires interactions between viral surface proteins and cellular surface receptors and, in some case, also cellular coreceptors and the fact that the viral receptors are expressed in a tissue and/or species specific manner. The tropism, however, presents a limitation in the ability to use viral vectors for gene therapy if intended target cells are not viral native host cells. It is difficult to transfect recombinant viruses to cells lacking these receptors. Therefore, studies of viral receptor expression, receptor-virus interaction and mechanism of viral entry is very important to gene therapy research.

In the case of adenovirus, infection by adenovirus requires binding of viral fiber protein to the extracellular domains of a recently identified 46-kD membrane protein named coxsackievirus/adenovirus receptor (CAR) (Bergelson, et al., 1997, Science 275, 1320–3.). Fiber is a trimer with a structure similar to a knob. The interaction between CAR and viral fiber is highly specific, and of high affinity (Louis, et al., 1994, J Virol 68, 4104–6, Bergelson, et al., 1998, J Virol 72, 415–9.). The structure of the fiber knob in complex with extracellular domain of CAR has been delineated recently (Bewley, et al., 1999, Science 286, 1579–83, Roelvink, et al., 1999, Science 286, 1568–71.). The identified binding site for CARs is on the side of the fiber knob with three CAR monomers bound per fiber knob trimer. The multivalency of CAR binding may contribute to the high efficiency of adenovirus infection. Following initial binding, the viral protein penton base binds via its Arg-Gly-Asp (RGD) motif to $\alpha_v\beta_3$ or $\alpha_v\beta_5$ integrins of cell membrane and this binding activates virus internalization via receptor-mediated endocytosis (Wickham, et al., 1993, Cell 73, 309–19.). Inside coated vesicles conformational changes of viral protein trigger the passage of adenovirus core particle through the cell membrane (Wickham, et al., 1994, J Cell Biol 127, 257–64, Wang, et al., 1998, J Virol 72, 3455–8.). Both high affinity binding by adenovirus and endocytosis events by the host cells are necessary for the adenoviral transfection to occur. Because of its ability to transfect a variety of quiescent tissues or cells and to maintain a long-term transgene expression adenovirus has been preferred over other available gene delivery systems for gene therapy. In fact, a majority of clinical trials currently underway use recombinant adenoviral vector based gene delivery systems.

Retroviruses are another example in which presence of viral receptors on host cells are critical for viral entry. Retrovirus infects cells in a two step mechanism. These viruses contain two envelope glycoprotein subunits designated surface (SU) and transmembrane (TM) which form an oligomeric complex on the viral surface and mediate viral entry. The SU protein contains the viral receptor binding determinants whereas the TM protein contains a hydrophobic transmembrane region and a separate hydrophobic segment that mediates virus-cell membrane fusion (Weiss, 1993, The Retroviridae 2, 1–107.). The first step of infection is the attachment of the viral particle via the surface protein of the retrovirus envelope (env) protein and that is followed by viral and cellular membrane fusion for viral uptake. The env protein is largely responsible for the tissue or species specificity of the retroviral infectivity. In the infection by human immunodeficiency virus (HIV), the soluble cell surface receptor is CD4 membrane protein. While G protein-coupled chemokine receptors, such as CXCR4 or CCR5, each acts as coreceptors for the syncytium-inducing T-cell tropic X4 strains (Feng, et al., 1996, Science 272, 872–7.) and primary non-syncytium-inducing macrophage tropic R5 strains, respectively (Deng, et al., 1996, Nature 381, 661–6.). It is also evident that many primary HIV isolates are in fact dual tropic, having the ability to utilize both CXCR4 and CCR5 as coreceptors, and are named as R5X4 isolates.

Another example is adeno-associated viruses (AAV). AAV has a linear single-stranded DNA and only undergo productive infection if the infected cells are co-infected with a helper virus (e.g., adeno- or herpesvirus) otherwise the genome becomes integrated in a latent state at a specific site on a human chromosome (Bems, 1996, Fields Virology.). Recombinant adeno-associated viruses are typically made by replacing viral genes with desired genes of interest or by simply adding the terminal AAV DNA sequences (ITRS) to these genes. In the case of type 2 AAV, membrane associated heparan sulfate proteoglycan is a receptor for viral infection (Summerford and Samulski, 1998, J Virol 72, 1438–45.).

Other examples include negative strand RNA viruses. These viruses infect cells by a variety of different mechanisms. For example, Influenza A viruses which have a segmented RNA genome, contain a surface hemagglutinin protein which binds to cell surface sialic acid receptors and mediates viral entry in a low pH endosome following receptor-mediated endocytosis (Lamb and Krug, 1996, Fields Virology.). The positive strand RNA viruses also infect cells by receptor mediated entry. For example, among the picomaviruses, different members of the immunoglobulin protein superfamily are used as cellular receptors by poliovirus, by the major subgroups of rhinoviruses, and by coxsackie B viruses, whereas an integrin protein is used by some types of ecoviruses and a low density lipoprotein receptor is used by minor subgroups of rhinoviruses (Rueckert, 1996, Fields Virology.). Following receptor binding, it is not yet fully understood what role receptor-mediated endocytosis plays for picomaviral entry, if indeed it is required. Paramyxoviruses containing a non-segmented RNA genome have two surface viral proteins, the hemagglutinin (HN) and fusion protein (F), required for viral entry which occurs at neutral pH. These viruses utilize sialic acid receptors, or protein receptors, such as CD46 used by measles virus, for viral entry (Lamb and Kolakofsky, 1996, Fields Virology.). Rhabdoviruses (e.g., VSV) also have a non-segmented RNA genome, contain a surface protein (G) which also binds to specific cell surface receptors and mediates viral entry in a low pH endosome. In some cases, however, a specific phospholipid, in steady of protein peptide, appears to be one of the receptors for VSV (Wagner and Rose, 1996, Fields Virology.). The herpesviruses which have large double-stranded DNA genomes, contain a number of surface glycoproteins involved in viral entry and utilize various cell surface receptors. For example, herpes simplex virus and cytomegalovirus entry involves binding to a heparin sulfate cell surface receptor and herpes simplex viruses use other proteins (e.g., HVEM) for viral entry (Montgomery, et al., 1996, Cell 87, 427–36.). In contrast, Epstein-Barr virus entry is initiated by binding to a completely distinct cell surface receptor, CR2 (Wolf, et al., 1993, Intervirology 35, 26–39.). Strategies have been described that allow one to engineer herpes simplex viruses, cytomegaloviruses and Epstein-Barr viruses as vectors for heterologous gene expression (Roizman, 1996, Proc Nail Acad Sci USA 93, 11307–12, Marconi, et al., 1996, Proc Natl Acad Sci USA 93, 11319–20.). Because the picornaviruses lack a surface lipid bilayer, their entry pathway does not involve fusion of a viral membrane with a host cell membrane. In contrast, the alphaviruses (e.g., Sindbis virus and Semliki virus) do contain a surface lipid bilayer. These viruses contain two (E1 and E2) surface proteins, and in some cases a third (E3) surface protein important for viral entry. These viruses use various cell surface receptors. For example, Sindbis virus can use a laminin receptor or other receptors and generally enter cells by a pH-dependent mechanism, following receptor-mediated endocytosis (Schlesinger and Schlesinger, 1996, Fields Virology.). A pseudotyped virus has the env protein from a first retrovirus of a desired specificity and core or structural proteins from a second virus (e.g. a second retrovirus, an orthomyxovirus or a rhabdovirus). Viral pseudotypes have been described (Landau, et al., 1991, J Virol 65, 162–9, Dong, et al., 1992, J Virol 66, 7374–82, Le Guern and Levy, 1992, Proc Natl Acad Sci USA 89, 363–7.). A pseudotyped virus can be targeted to specific cell-types for viral entry in using a receptor mediated process. Poxviruses have large double stranded DNA genomes and enter cells by a pH independent mechanism via receptors that remain to be defined (Moss, 1996, Fields virology.). Poxvirus vectors have been used extensively for the expression of heterologous recombinant genes and as vaccines (Moss, 1996, Proc Natl Acad Sci USA 93, 11341–8, Paoletti, 1996, Proc Natl Acad Sci USA 93, 11349–53.).

In summary, various viral species mentioned above gain entry into host cells through specific cellular membrane receptors. In some cases, the membrane receptors have been identified, i.e., CD4 for HIV, CAR for adenovirus, etc. In other cases, the specific membrane protein or peptide that serves as viral receptor for viral entry has not been identified.

Recombinant adenoviral vectors are generated by a variety of techniques that include introducing a desired gene of interest into a bacterial plasmid at a site flanked by sequences that provide control elements for gene expression. These sequences are further flanked by DNA sequences from adenovirus. These sequences from adenovirus serve as sites for recombination with a compatible adenoviral genome when co-transfected together into an appropriate mammalian cell line (Horwitz, 1996, Fields Virology.).

However, to be safely and effectively used in gene therapy it is necessary to increase the viral transfection efficiency and selectivity. This is also true for adenoviral based gene delivery due to a broad low-level, non-uniform expression of CAR (Wickham, et al., 1996, J Virol 70, 6831–8.). Two major approaches have been underway to increase the transfection efficiency and selectivity. The first approach has been to modify the viral fiber protein by fusing specific peptides to the viral fiber. For example, a stretch of peptides specific for high affinity integrin $\alpha_v$ binding or heparan sulfate-containing receptor binding were inserted into fiber protein (Wickham, et al., 1997, J Virol 71, 8221–9.). These modifications significantly increased the viral transfection efficiency in malignant glioma cell lines (Staba, et al., 2000, Cancer Gene Ther 7, 13–9.). Similarly, fusing a peptide from adenovirus serotype 35 to the adenovirus serotype 5 capsid protein also increased viral transfection efficiency in CD34+ hematopoietic stem cells (Shayakhmetov, et al., 2000, J Virol 74, 2567–83.). Although these approaches have increased transfection efficiency of recombinant adenovirus in certain tissue, they generally widen rather than narrow the viral tropism because they do not block the viral transfection into its native hosts. In fact, these approaches by their nature are limited in their ability to modify fiber protein because conformational changes in fiber protein may affect its binding to CAR and subsequent viral propagation. The second approach has been to use a protein ligand to re-direct the recombinant adenovirus to selected tissue. In one of such experiment, an adenovirus neutralizing antibody was fused with the epidermal growth factor (EGF) (Watkins, et al., 1997, Gene Ther 4, 1004–12.) and the fusion protein re-directed recombinant adenovirus to EGF receptor-expressing cells. The limitation of this approach is its ability to be adapted for broad applications to other cell markers since not all surface markers have their native ligands. A cross-linking technique was also described in which viral particles were linked to specific antibodies (Rogers, et al., 1997, Gene Ther 4, 1387–92.). However, these approaches failed to block the infection of native host cells by recombinant adenovirus. Using bispecific antibodies which recognized both a FLAG tag inserted on the penton base of adenovirus and $\alpha_v$ integrin (or E-selectin) expressed on host cells, recombinant adenovirus particles were re-directed specifically to $\alpha_v$ integrin (or E-selectin) expressing cells (Wickham, et al., 1997, Cancer Immunol Immunother 45, 149–51.). This strategy also did not block the native host infection.

In the effort to target retrovirus in gene therapy, similarly strategy using a fusion protein ligand has also been reported recently. In one of such approach that is similar to the use of antibody fusing to EGF as a bispecific ligand to link virus to EGF receptor (Watkins, et al., 1997, Gene Ther 4, 1004–12.), the viral cellular receptor for retrovirus was used in replacement of an antibody species to be fused to EGF (Snitkovsky and Young, 1998, Proc Natl Acad Sci USA 95, 7063–8.). This fusion protein also demonstrated ability to target retrovirus to EGF expressing cells (Snitkovsky and Young, 1998, Proc Natl Acad Sci USA 95, 7063–8.). This finding was awarded a U.S patent (U.S. Pat. No. 6,060,316). However, like in the case to target recombinant adenovirus, employ EGF in fusion protein in targeting lacks flexibility. It also is limited to only EGF receptor expressing cells. Although EGF receptor is highly expressed on some tumor cells normal cells also express this receptor. Therefore, this strategy is not highly selective and not specific enough for safety reason if recombinant virus carrying a cytotoxic gene is used.

It would be highly desirable to be provided with means to block the native viral infection and target the virus with high selectivity so that when recombinant viral based vectors are used in clinical or experimental settings nonspecific and undesired viral infection does not occur.

It would be highly desirable to be provided with means to re-target recombinant viruses specifically to desired tissue with high efficiency so that the viral titer in gene delivery that is required to achieve therapeutic value is reduced in clinical or experimental settings. This step can be especially beneficial because reduced viral titer can reduce adverse effects.

It would also be highly desirable to be provided with means to target recombinant viruses with great flexibility and in a easily adaptable manner so that the targeting system can be adaptable to many different tissue or cell of interest and applicable in many conditions under clinical and experimental settings. This feature can be especially useful in broad applications.

SUMMARY OF THE INVENTION

The current invention relates to a novel targeting method for gene delivery by recombinant viruses. The recombinant viruses are targeted to any cells by a fusion protein ligand in coupling with a specific antibody species. The specific antibody is a monoclonal antibody which recognizes a specific antigenic determinant on the surface of an antigen or a purified polyclonal antibody which recognizes many different antigenic determinants on the surface of an antigen. In current targeting method, one end of the fusion protein ligand is the extracellular domain of a viral receptor that binds specifically to the surface of a virus while the other end is a IgG Fc-binding protein, such as protein A from bacteria, that binds specifically to the Fc region of an antibody. Antibody used is specific recognizing a cell surface marker that is present on the surface of target cells. The serial specific binding interactions, i.e., binding of the virus to fusion protein, fusion protein to antibody and antibody to cell surface marker, bring the recombinant viruses that contain a heterologous gene or genes encoding therapeutic protein(s) to the surface of target cell followed by viral entry in target cell.

In current invention, the interaction between a viral receptor and a viral species is specific (e.g., CAR binding to the fiber protein of adenovirus, and CD4 molecule binding to the gp120 protein of human immunodeficiency virus). The interaction between antibody and cell surface marker is also specific (e.g., anti ICAM-1 IgG binding to ICAM-1 molecules wherever it is expressed, and anti CD34 IgG binding to CD34 molecules). However since the Fc regions of all antibody species are structurally similar and can bind to the IgG Fc-binding protein, this feature makes the IgG Fc-binding protein of the fusion protein ligand capable to bind to any given antibody species. Because of this ability, fusion protein ligand in current invention can bind to different antibody species that recognizes different specific cell surface markers on different target cells. In this regard, current invention not only circumvents the requirement for expression of viral receptors on target cells but also circumvents the requirement for the presence of cellular receptors, such as EGF receptor (Snitkovsky and Young, 1998, Proc Natl Acad Sci USA 95, 7063–8.), on target cells, and co-presence of native peptide or protein ligands, such as EGF, for binding to the receptor (Snitkovsky and Young, 1998, Proc Natl Acad Sci USA 95, 7063–8.). In these prior arts targeting via the fusion proteins comprising EGF as a means to target EGF receptor expressing cells by Watkins for delivery of recombinant adenovirus (Watkins, et al., 1997, Gene Ther 4, 1004–12.) or by Snitkovsky for delivery of recombinant retrovirus ((Snitkovsky and Young, 1998, Proc Natl Acad Sci USA 95, 7063–8.) and U.S. Pat. No. 6,060,316), requires that EGF receptor is expressed on target cells in order for such delivery.

One aim of the present invention is to provide means to block the native viral infection and target the virus with high selectivity so that when recombinant viral based vectors are used in clinical or experimental settings nonspecific and undesired viral infection does not occur.

Another aim of the present invention is to re-target recombinant viruses specifically to desired tissue with high efficiency so that the viral titer in gene delivery that is required to achieve therapeutic value is reduced in clinical or experimental settings. This step can be especially beneficial because reduced viral titer can reduce adverse effects.

Another aim of the present invention is to target recombinant viruses with great flexibility and in a easily adaptable manner so that the targeting system can be adaptable to many different tissue or cell of interest and applicable in many conditions under clinical and experimental settings. This feature can be especially useful in broad applications.

BRIEF DESCRIPTION OF THE DRAWINGS

Drawing 1 Schematic drawing of overall targeting strategy. The native infective pathway of adenovirus is through interaction with CAR (1). In the presence of CAR/Hg/Pro-A ligand the native infective pathway of adenovirus to CAR is blocked (2). Moreover, in the presence of a specific antibody species, the CAR/Hg/Pro-A and antibody complex re-direct adenovirus to target cell that expresses a surface marker recognized by the antibody (3).

Drawing 2 Construction procedures for plasmid that producing fusion CAR/Hg/Pro-A protein ligand in yeast. The names of each plasmid are underlined and technical procedures during subcloning steps for making final construct are numbered and placed in box. Arrows with dashed lines indicate products of each step. DNA components on the plasmid are either labeled nearby or indicated with a small arrow. Restriction sites used during constructions are indicated as well. Details of each construction procedure are given in the EXAMPLES.

Figure 1:
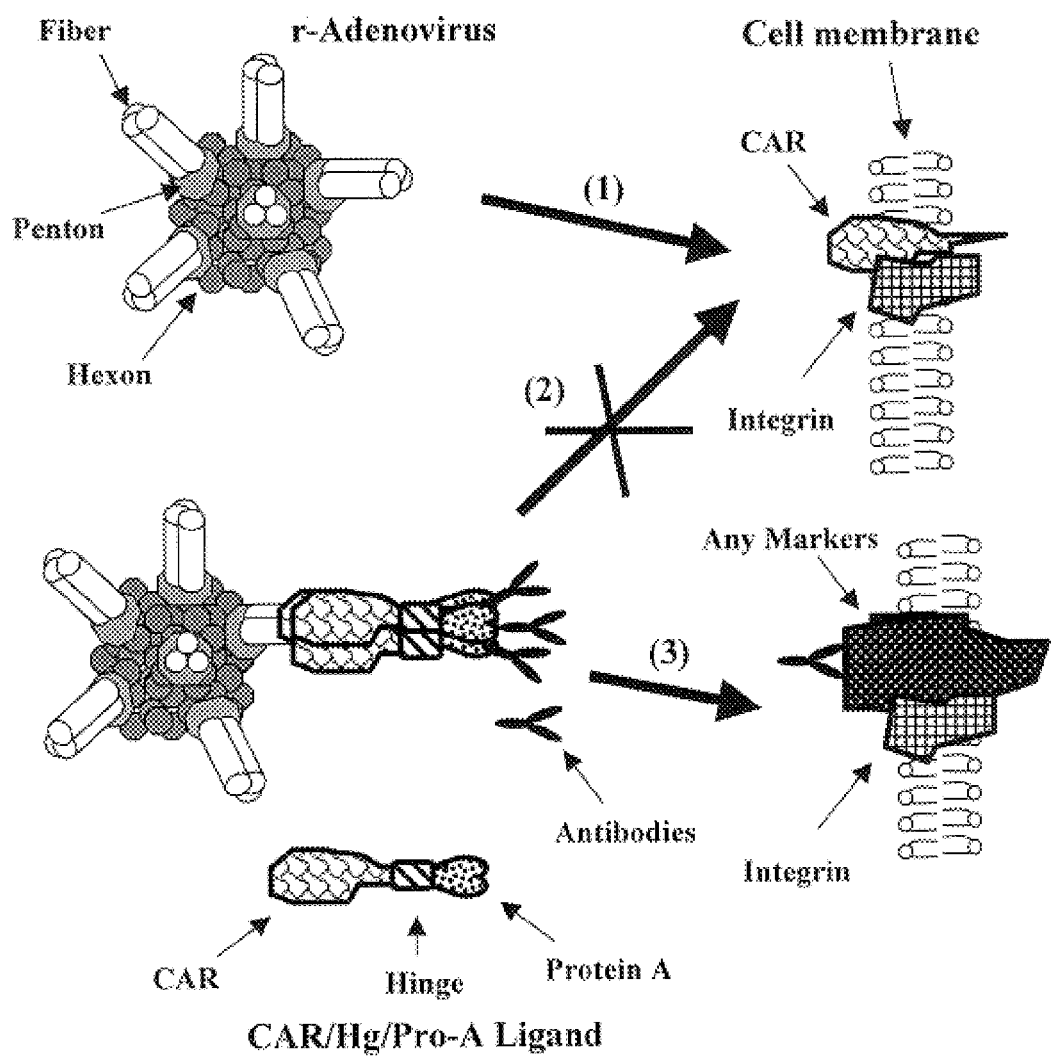

Drawing 3A Structure of the chimeric CAR/Hg/Pro-A gene in pPICα-CAR/Hg/Pro-A plasmid (linearlized for presentation). The chimeric CAR/Hg/Pro-A gene encodes CAR/Hg/Pro-A fusion protein ligand (expended). The alpha secretary factor (represented by a filled box and indicated with an arrow) is at amino terminus of CAR/Hg/Pro-A and is removed from the fusion protein ligand by endopeptidase in yeast culture. The hinge region is also represented by a filled box and is indicated with an arrow. The myc tag and six-histidine tag (also represented by a filled box and indicated with an arrow) are present at carboxyl terminus. 5'AOX1 (hatched box) is a yeast promoter while AOX1TT (represented by a box with small black/white squires) contains the transcriptional termination signal. The zeocin expression cassette (a long filled heavy bar) is the selectable marker in both bacteria and yeast that harbors the plasmid. The single line represents plasmid sequence for replication in bacteria (ColE1 origin). The chimeric CAR/Hg/Pro-A gene was inserted in the yeas specific expression cassette between 5'AOX1 and AOX1TT.

Drawing 3B Amino acid sequence (SEQ ID NO:8) of entire protein synthesized from chimeric CAR/Hg/Pro-A gene in transfected yeast colonies. The sequence starts with an α-secretable factor at amino terminus, is followed by CAR/Hg/Pro-A fusion protein ligand and ends with myc, six-his tags at carboxyl terminus. The amino acid sequence of CAR/Hg/Pro-A ligand is in bald.

Drawing 3C SDS-polyacrylamide gel electrophoresis (PAGE) of CAR/Hg/Pro-A ligand harvested from yeast culture medium. The protein ligand after SDS-PAGE was transferred to nitrocellulose membrane and was hybridized with anti myc tag IgG for visualization (lane 1). This demonstrated the specificity of the protein ligand. In another case, the protein ligand after SDS-PAGE was stained with Coomassie blue (lanes 2 and 3). In lane 2, 4.5 µg purified CAR/Hg/Pro-A fusion protein ligand was loaded to demonstrate the purity of this protein that was used in the experiments. In lane 3, however, crude concentrated (about 5-fold) culture medium was loaded to demonstrate efficiency of purification procedures. In all three lines, a band migrating at approximately 45 kilo Dolton, corresponding to the estimated molecular weight of CAR/Hg/Pro-A protein ligand, was identified.

Drawing 4 Induction of ICAM-1 expression in TNF-α treated cultured human umbilical vascular endothelial cells (HUVEC). The level of ICAM-1 expression was assessed using an immunoassay described by Zund et al (Zund, et al., 1996, Proc Natl Acad Sci USA 93, 7075–80.). Briefly, cells, at different time points after TNF-α treatment (0.1 µg/ml, purchased from Calbiochem, La Jolla, Calif.), were fixed. Purified mouse monoclonal antibody against human ICAM-1 (purchased from PharMingen, San Diego, Calif.) was used as primary antibody in immunostaining. After washing, cells were incubated with horseradish peroxidase (HRP)-conjugated rat anti mouse IgG and peroxidase substrate, 2,2'-azino-dis(3,ethylbenz-thiazoline-6-sulphonic acid). The intensity of blue color developed was measured quantitatively at 405 nm with a plate spectrophotometer. Expression of ICAM-1 was significantly induced in cultured HUVEC from 4 hours (**$p<0.01$) after TNF-α treatment.

Drawing 5 Transfection efficiency of Ad5GFP (a recombinant adenovirus species that expresses green fluorescence protein in transfected host cells) in untreated normal or TNF-α treated (for 24 hours), ICAM-1 expressing HUVEC. Forty-eight hours after Ad5GFP transfection, green fluorescence was measured quantitatively by a plate fluorescent-photometer to determine the viral transfection efficiency. At higher multiplicities of infection (MOI), i.e., 10.8, 43.8, and 175.0, normal cells are significantly more sensitive to Ad5GFP transfection.

Drawing 6 Blocking of Ad5GFP-mediated gene transfection by CAR/Hg/Pro-A (shortened and marked as FP) in normal untreated endothelial cells. Transfection efficiency was determined with the same method as was used in Drawing 5. When CAR/Hg/Pro-A ligand was added in the viral transfection mixture at a concentration of 7.6 ng/µl, the transfection efficiency by Ad5GFP (MIO=43.8) was reduced by 29% ($p<0.01$) whereas at higher ligand concentration (26.7 ng/µl), it was reduced by 58% ($p<0.01$). In both cases addition of BSA (bovine serum albumin) as controls did not decrease the transfection efficiency.

Drawing 7 Re-directing Ad5GFP with CAR/Hg/Pro-A ligand (marked as fusion protein) in complex with anti ICAM-1 IgG to normal (top panel; viral MOI=43.8) or TNF-α treated, ICAM-1 expressing (bottom panel; viral MOI=175) HUVEC. In normal endothelial cells, the presence of Ad5GFP, CAR/Hg/Pro-A ligand and anti ICAM-1 IgG complex did not increase the viral transfection efficiency whereas in TNF-α treated cells, the presence of Ad5GFP, CAR/Hg/Pro-A and anti ICAM-1 IgG complex dramatically increased transfection efficiency by several folds. This increase of transfection efficiency is specific because lack of CAR/Hg/Pro-A ligand or anti ICAM-1 IgG or replacement of anti ICAM-1 IgG with mouse non specific IgG did not have this effect (*$p<0.05$;**$p<0.01$).

Drawing 8 (Parts A–F) Photographical images of TNF-α treated, Ad5GFP transfected HUVEC under light microscopy (B, D and F) and under fluorescent microscopy (A, C and E). In a volume of 30 µl, cells in culture were infected with Ad5GFP alone (A, B), Ad5GFP in the presence of 0.2 µg fusion protein (C, D), Ad5GFP in the presence of 0.2 µg fusion protein and anti ICAM-1 IgG (E, F). Please note that all photos were taken with the same exposure time.

DETAILED DESCRIPTION OF THE INVENTION

To achieve specific gene targeting using a recombinant virus, a novel strategy is developed and it is depicted in Drawing 1 using adenovirus as an example to demonstrate the strategy. However, any extracellular domain of a viral receptor that is a membrane protein or membrane peptide can be used to replace extracellular domain of CAR (Drawing 1) and can be inserted as a part of the fusion protein ligand for targeting. Under native viral infection pathway, adenovirus infects its target cells by binding via its fiber protein to the viral receptor, CAR, on the cell membrane (Drawing 1, step (1)) and the binding trigs a series reactions that end with viral entry in host cells. Thus recombinant CAR can be used specifically to block the viral interaction with native CAR. To achieve cell type specific gene targeting the extracellular domain of CAR is cloned and fused at its carboxyl terminus to a IgG Fc-binding protein. This protein is a portion of Protein A and contains two IgG Fc-binding sites (designated as Pro-A in Drawing 1) and is cloned from staphylococcus (Deisenhofer, 1981, Biochemistry 20, 2361–70.). Protein A is known for high affinity binding to the Fc region of antibodies. Many other proteins also contain IgG Fc-binding activity. These proteins can also be used to replace Protein A in the fusion protein ligand. Genes that encode Protein G, Protein I from bacterial sources, or other genes encoding proteins containing activity to bind to Fc region of IgG, such as cell Fc receptor, can also be used here. Peptides that are designed by random combination of genetic codes, and are expressed on the surface of phage, bacterial or yeast by DNA transfection, can be identified by screening phage, bacterial or yeast libraries for IgG Fc-binding activity. These peptides can also be used to replace Protein A for the IgG Fc-binding.

To minimize the mutual effects between CAR and Pro-A in protein folding, another feature in current invention is to insert a short DNA fragment that encodes the hinge region of mouse IgG3 (Pack and Pluckthun, 1992, Biochemistry 31, 1579–84.) between CAR and Pro-A. Thus in the fusion protein ligand, Pro-A provides high affinity binding to antibody. Antibodies that bind to the Protein A on the fusion protein ligand will define the specificity of target cell. When adenovirus binds to fusion protein ligand, CAR/Hg/Pro-A, and ligand binds to an antibody that recognizes a specific cell surface marker, the recombinant adenovirus will be targeted to and infect the cell as illustrated in Drawing 1.

In this embodiment, the current invention is a novel targeting method. In this method a recombinant virus can be targeted to any specific cell-type by contacting cells with a recombinant virus through a fusion protein ligand which comprises not only a viral receptor to bind to the virus but also an IgG Fc-binding protein for an antibody. The virus binds to the extracellular domain of viral receptor on the fusion protein ligand and the fusion protein ligand binds to the Fc region of an antibody species. Thus, fusion protein ligand in coupling with an antibody species can bring the virus sufficiently close to the membrane of the target cell and to activate the membrane fusion process, and infection when the target cells express a specific cell surface marker and the marker is recognized by the antibody. Using different antibodies, the recombinant viruses are targeted to different cells. The virus can include in its genome a heterologous nucleic acid sequence encoding a desired protein.

Cellular receptors made at least in part by membrane proteins or peptides are involved in viral infection in following viral species. Except adenovirus, viruses included in this category are retrovirus, parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus. Other double stranded DNA viruses besides adenovirus including herpesvirus (e.g., Herpes Simplex virus types 1 and 2, Epstein-Barr virus, cytomegalovirus), and poxvirus (e.g., vaccinia, fowlpox and canarypox). Other viruses are Norwalk viruses, togaviruses, flaviviruses, reoviruses, papovaviruses, hepadnaviruses, and hepatitis viruses. Examples of retroviruses include avian leukosis-sarcoma viruses (e.g., avian leukosis viruses, avian sarcoma viruses), mammalian C-type, B-type, D-type retroviruses, HTLV-BLV viruses, lentiviruses, spumaviruses (Coffin, 1996, Fundamental Virology.). Others include murine leukemia viruses, murine sarcoma viruses, mouse mammary tumor viruses, bovine leukemia viruses, feline leukemia viruses, feline sarcoma viruses, avian leukemia viruses, human T-cell leukemia viruses, baboon endogenous viruses, Gibbon ape leukemia viruses, Mason Pfizer monkey viruses, simian immunodeficiency viruses, simian sarcoma viruses, Rous sarcoma viruses and lentiviruses.

Viral species stated above target host cells via a cellular receptor or receptors that have been identified or have not been unidentified yet. The extracellular, soluble domains of viral receptor can be cloned in a conventional way. The cloned extracellular, soluble domain of these receptors can be used to replace the CAR in the fusion protein ligand. These extracellular, soluble domains of receptor when employed in the fusion protein ligands provide a binding site to recombinant viruses and block the virus to contact with their native receptors on the host cells. These extracellular, soluble domains of cellular receptor are fused with a protein domain that binds to Fc region of antibody directly or indirectly via a short peptide encoding a hinge region of an antibody. The protein domain with Fc-binding activity is a peptide segment containing two binding sites for antibody Fc region. In some cases, the segment from protein A can be replaced with other similar protein domain, such as IgG Fc-binding domain from Protein I or Protein G. In yet another case, this segment can be replaced with cellular membrane receptor for antibody Fc region. The fusion protein ligand in current invention is a bispecific ligand that when coupled with an antibody species binds to viruses through its cellular receptor and at the same time through its interaction with antibody binds to a cell surface marker. These actions by fusion protein ligand bring the viruses close to the target cells and results in viral entry into host cells.

The viral vectors employed in the present invention can be used for polynucleotide or gene delivery to a specific cell-type or tissue. The polynucleotide to be delivered to the cell or animal can include a polynucleotide native to the viral vector or heterologous to the vector. Generally, the polynucleotide is present or has been incorporated into the genome of the viral vector. In a preferred embodiment, the viral vector has been engineered to contain a polynucleotide which is itself therapeutic agent or encodes a heterologous therapeutic protein. An example of a therapeutic polynucleotide includes RNA (e.g., ribozymes) and antisense DNA that prevents or interferes with the expression of an undesired protein in the target cell. Examples of therapeutic proteins include antigens or immunogens such as a polyvalent vaccine, cytokines, tumor necrosis factor, interferons, interleukins, adenosine deaminase, insulin, T-cell receptors, soluble CD4, epidermal growth factor, human growth factor, blood factors, such as Factor VIII, Factor IX, cytochrome b, glucocerebrosidase, ApoE, ApoC, ApoAI, the LDL receptor, negative selection markers or "suicide proteins", such as thymidine kinase (including the HSV, CMV, VZV TK), anti-angiogenic factors, Fc receptors, plasminogen activators, such as t-PA, u-PA and streptokinase, dopamine, MHC, tumor suppressor genes such as p53 and Rb, monoclonal antibodies or antigen binding fragments thereof, drug resistance genes, ion channels, such as a calcium channel or a potassium channel, and adrenergic receptors, and intracellular proteins which is a component transducting intracellular signals or a component to carry out cellular apoptosis (cellular suicide), or a components to inhibit signal transduction or to inhibit cellular apoptotic process, etc.

As set forth above, the fusion protein ligand binding on the viral surface binds to a surface marker on the target cell through an antibody species. A target cell is defined herein as a cell which is intended to be infected by the virus possessing the fusion protein ligand in coupling with an antibody species on the viral surface. Typically, the target cell is of animal origin and can be a stem cell or somatic cell. Suitable animal cells can be of, for example, mammalian or avian origin. Examples of mammalian cells include human, bovine, ovine, porcine, murine, rabbit cells. The cell may be an embryonic cell, bone marrow stem cell or other progenitor cell. Where the cell is a somatic cell, the cell can be, for example, an epithelial cell, fibroblast, smooth muscle cell, blood cell (including a hematopoietic cell, red blood cell, T-cell, B-cell, etc.), tumor cell, cardiac muscle cell, macrophage, dendritic cell, neuronal cell (e.g., a glial cell or astrocyte), or pathogen-infected cell (e.g., those infected by bacteria, viruses, virusoids, parasites, or prions). Typically, cells isolated from a specific tissue (such as epithelium, fibroblast or hematopoietic cells) are categorized as a "cell-type." The cells can be obtained commercially or from a depository or obtained directly from an animal, such as by biopsy. Alternatively, the cell needs not be isolated at all from the animal where, for example, it is desirable to deliver the virus to the animal in gene therapy.

Cells are typically characterized by markers expressed at their surface that are termed "specific markers". These specific markers include surface proteins, such as cellular receptors, adhesion molecules, transporter proteins, components of the extracellular matrix and the like. These markers, proteins and molecules also include specific carbohydrates and/or lipid moieties, for example, conjugated to proteins. The bispecific fusion protein ligand binding on the viral surface binds via a specific antibody species to one or more surface proteins on the target cell. The markers on the target cell surface can be tissue- or cell-type specific or can be found on the surface of many cells. The surface marker made by a protein or protein peptide is a transmembrane protein receptor with one or more domains which extend to the exterior of the cell (e.g. the extracellular domain). Where cell-type specific delivery is desired (as in in vivo delivery of a viral vector), the surface protein selected for targeting is preferably specific to the tissue. By "specific" to the tissue, it is meant that the protein be present on the targeted cell-type but not present (or present at a significantly lower concentration) on a substantial number of other cell-types. The specific cell surface marker while being selected for targeting needs to be recognized by an antibody species. The selected antibody species recognize specifically the cellular surface marker. The Fc region of selected antibody species binds to the fusion protein ligand through its Fc binding domain. The fusion protein ligand on the viral surface when coupled with this specific antibody species connect the viruses to the specific cellular surface marker and mediate the viral entry or infection into these cells. In the example of in vitro gene delivery, where a specific type of cell or cell types, are contacted with a virus in pure or substantially pure form, specific delivery is set by the specificity of antibody and antigen interactions. Many different antibody species are available through many commercial laboratories that are specific against a particular cell surface marker.

As set forth above, the surface marker can be a cellular receptor or other cell surface protein. Examples of these receptors or proteins include receptors for cytokines, growth factors, and include, in particular epidermal growth factor receptors, platelet derived growth factor receptors, vascular endothelial growth factor receptors (Flk receptors), interferon receptors, insulin receptors, proteins with seven transmembrane domains including chemokine receptors and frizzled related proteins (Wnt receptors), immunoglobulin-related proteins including MHC proteins, CD4, CD8, ICAM-1, etc., tumor necrosis factor-related proteins including the type I and type II TNF receptors, Fas, DR3, DR4, CAR1, etc., low density lipoprotein receptor, integrins, and, in some instances, the Fc receptor. Other examples of surface proteins include cell-bound tumor antigens. Many antibody species against these surface proteins are commercially available and/or have been characterized in the art, including the mapping of the region involved in antigen-antibody binding. Cytokine and chemokine receptors are reviewed (Miyajima, et al., 1992, Annu Rev Immunol 10, 295–331, Murphy, 1994, Annu Rev Immunol 12, 593–633.). As set forth above, to activate or otherwise induce steps for viral entry and thus, infection, a bispecific fusion protein ligand in coupling with a specific antibody species can be added simultaneously with viruses to a cells or tissues that express specific surface markers which are recognized by the antibody species.

As set forth above, the bispecific fusion protein ligand binds to a specific surface marker via a specific antibody species. Typically, the antibody species is selected because it is specific for the target cell. Although it is not necessary, the cell surface marker selected, preferably, possesses the similar character as the native viral receptor. For example, adenoviral entry requires that the cellular receptor for adenovirus undergoes endocytosis and the targeting marker that is recognized by the antibody species preferably also undergo endocytosis to ensure high efficiency for gene delivery.

The extracellular, soluble domain of viral receptor in the fusion protein ligand is cloned from entire or a portion of extracellular domain of viral receptor. The viral binding portion can have an amino acid sequence which is the same or substantially the same as an amino acid sequence of a native viral cellular receptors. Similar to cellular receptors, many of the corresponding ligands have been identified, sequenced and characterized, including the portions thereof which bind to the recombinant viruses to be targeted. The viral binding portion of the fusion protein ligand can, therefore, include the same or substantially the same sequence of the entire native extracellular domain of the viral receptor or a binding motif for the virus. Where the viral receptor used in the construction of fusion protein ligand is a polypeptide, each receptor or a portion of the receptor can be a conjugate or fused with antibody Fc-binding domain directly or indirectly via a hinge region of antibody. In such cases, the fusion protein ligand is manufactured according to known methods of recombinant DNA technology. For example, the fusion protein can be expressed by a nucleic acid molecule comprising sequences which code for both moieties, such as by a fusion gene.

EXAMPLES

I. Construction of a yeast-expressing plasmid for production of bispecific CAR/Hg/Pro-A fusion protein ligand:

1. Plasmid construction:

cDNA encoding extracellular domain (minus the signal peptide) of CAR was cloned from a human embryo kidney cell line, HEK293, by reverse transcription-PCR (Drawing 2, step (1)) with a set of primers that have a few base alterations, to generate EcoRI and NotI sites at the 5' (5' CAR primer: 5'-gtggaattcgccagaagtttgag-3') and 3'(3' CAR primer: taatggcggccgc-aattagtcc) ends of the amplified PCR products, respectively. The amplified 690-bp fragment was digested with EcoRI and NotI (step 2), and cloned into plasmid pcDNA3 (Drawing 2, underlined) at EcoRI and NotI sites (step (3) and (4), pcDNA3 was purchased from Invitrogen, Carlsbad, Calif.) to generate pcDNA3 -CAR. A 357-bp fragment containing two Fc binding sites of protein-A was PCR amplified from the plasmid pEZZ18 (step (5) and pEZZ18 was purchased from Amersham-Pharmacia Biotech, Piscataway, N.J.). A set of primers altered in a few bases to generate NotI and XbaI sites at 5' (5' Pro-A primer: cgatgcggccgcagacaacaaa) and 3' (3' Pro-A primer: gcgtctgattc-ggcgcctgag) ends, respectively, was used. The amplified fragment was digested with NotI and XbaI (6), and cloned 3' to the CAR gene (step (7) and (8)) to generate pcDNA3-CAR/Pro-A plasmid. A synthetic linker (upstream: ggccccgaaacgagcaccccgccgggcagcagcgc and down stream: ggccgcgctgctgcccggcggggtcgacggtt-tcgg) which encoded a hinge region of mouse IgG3 (Pack and Pluckthun, 1992, Biochemistry 31, 1579–84.) was inserted at the NotI site (9) to separate CAR and Pro-A sequences in frame to generate pcDNA3-CAR/Hg/Pro-A. The NotI site at the 3' end of the insert was retained and used as a restriction site marker to determine the orientation of the insert. The chimeric CAR/Hg/Pro-A gene was subsequently released by digestion with EcoRI and XbaI (10) from pcDNA3-CAR/Hg/Pro-A and was inserted into plasmid pPICα (step (11) and (12), pPICα was purchased from Invitrogen) for the final construct, pPICα-CAR/Hg/Pro-A (Drawing 2 and 3A).

2. Production and purification of recombinant CAR/Hg/Pro-A ligand from yeast culture:

The zeocin resistant plasmid pPICα-CAR/Pro-A was transfected into the *Pichia pastoris* strain X-33 by electroporation according to the protocol provided with the EasySelect Pichia Expression Kit (Invitrogen). Six zeocin resistant colonies were isolated and screened for high level secretion of CAR/Hg/Pro-A ligand in the culture medium. Briefly, yeast colonies were grown in 6 ml buffered complex glycerol medium (BMGY) in 50 ml-baffled flasks at 30° C. in a shaking incubator till the $OD_{600}$ reached about 2. Cells were harvested by centrifugation, and the pellets were resuspended to an $OD_{600}$ of 1.0 in fresh buffered complex methanol medium (BMMY) and returned to the incubator. Methanol was added to a final concentration of 2% in every 24 hours to induce the transgene expression. At 48 hour after induction, medium was harvested by centrifugation to get rid of yeast and the supernatants were concentrated 5 fold using a Centricon filter (10,000 MW cut-off, Millipore, Bedford, Mass.). Concentrated supernatants were resolved by 10% SDS-PAGE followed by Western hybridization with anti-myc antibody (Invitrogen). An expressed band of estimated molecular weight of 45 kD, was detected in every colonies. The colony with the highest band intensity (representing highest secretion level) was identified and further analyzed for the expression pattern. At intervals (8, 12, 24, 48, 72 and 96 hours) after starting methanol induction culture medium was taken for Western hybridization. It was found that the secreted fusion protein started to accumulate from 8 hours and reached a plateau at 12 hours in culture medium.

Figure 3A:
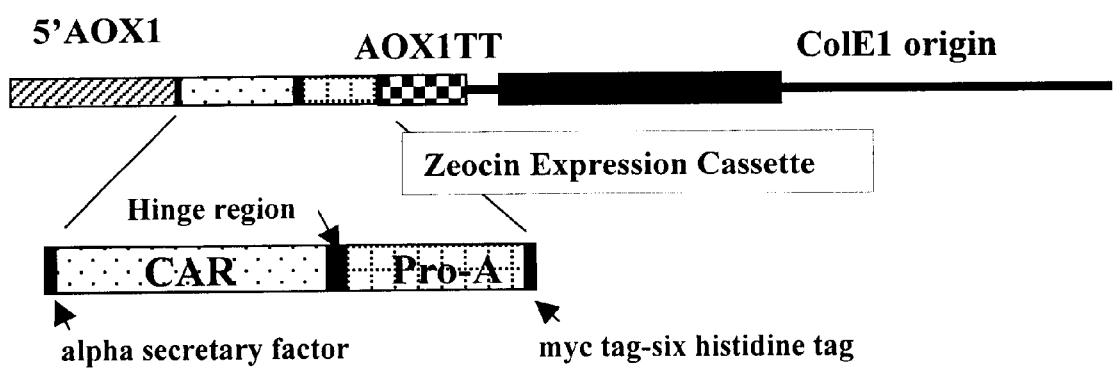
Figure 3C:
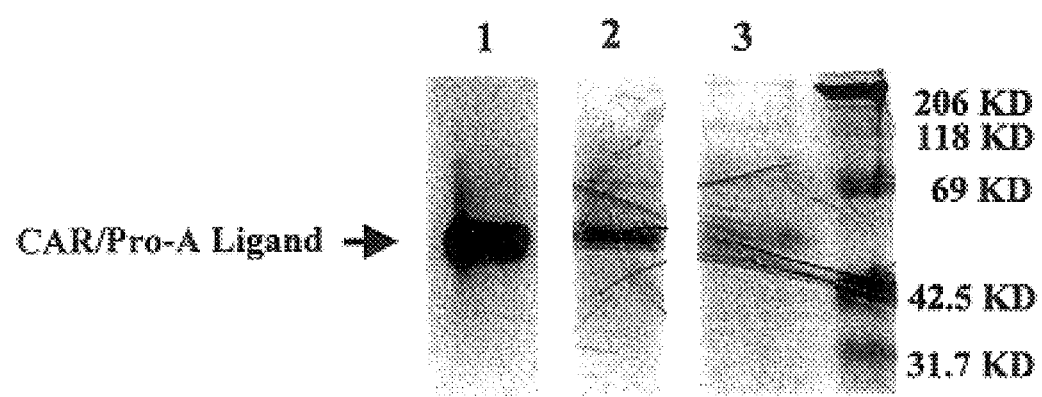
Figure 4:
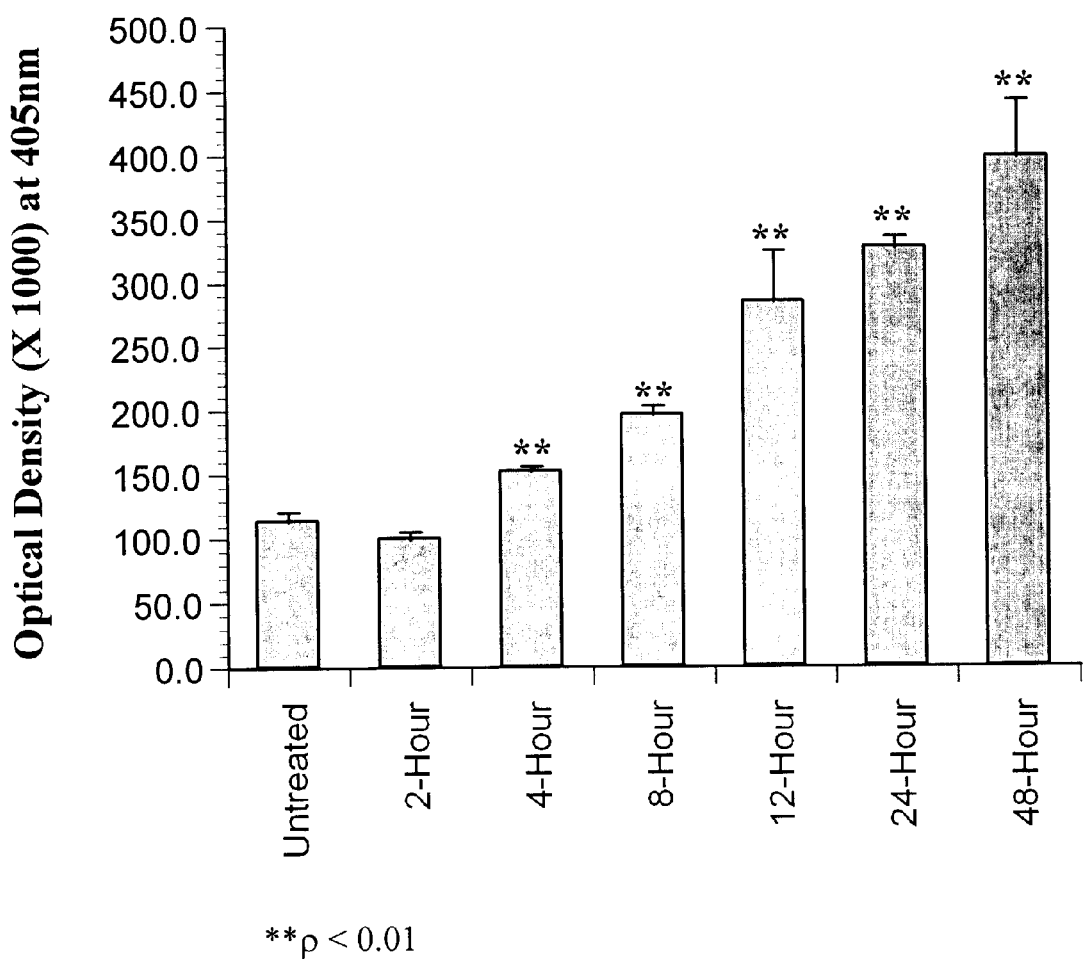
Figure 5:
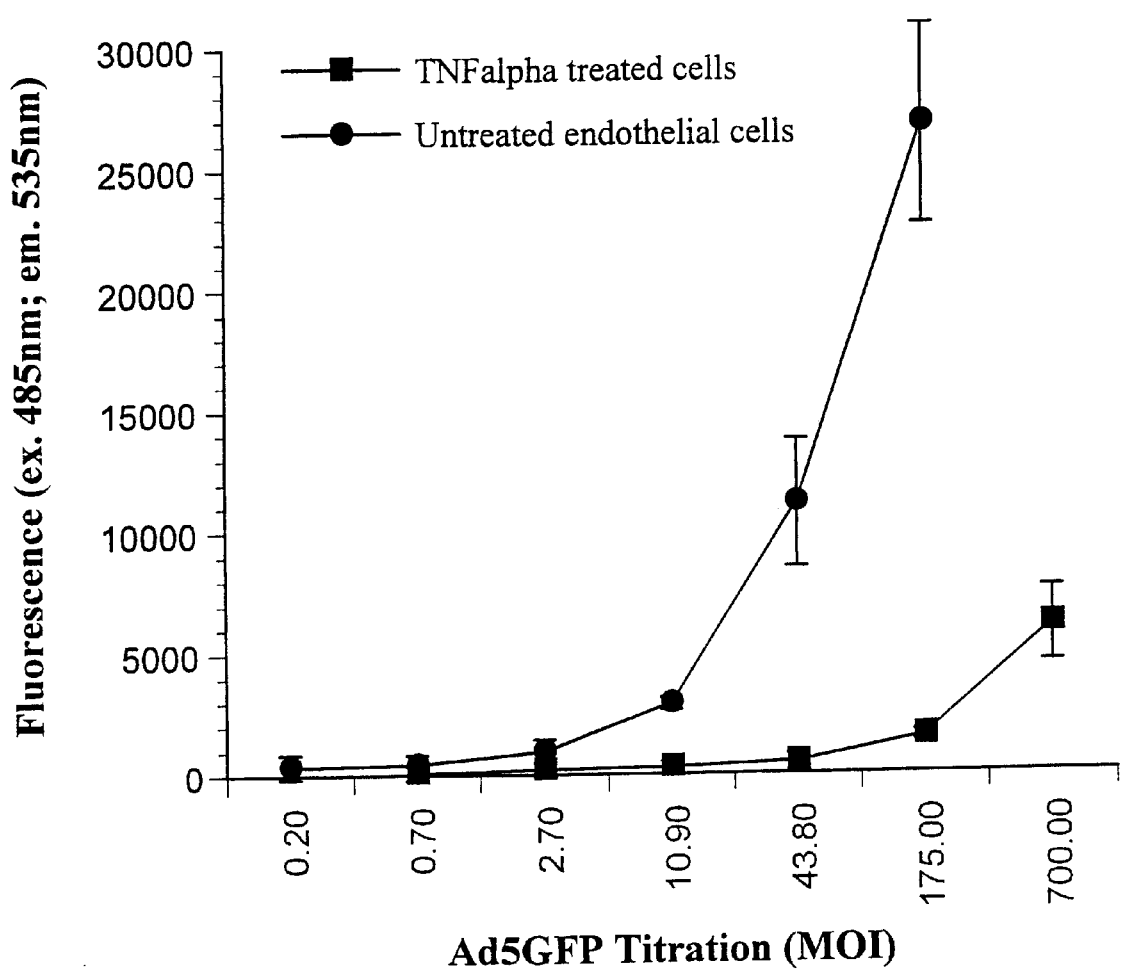
Figure 6:
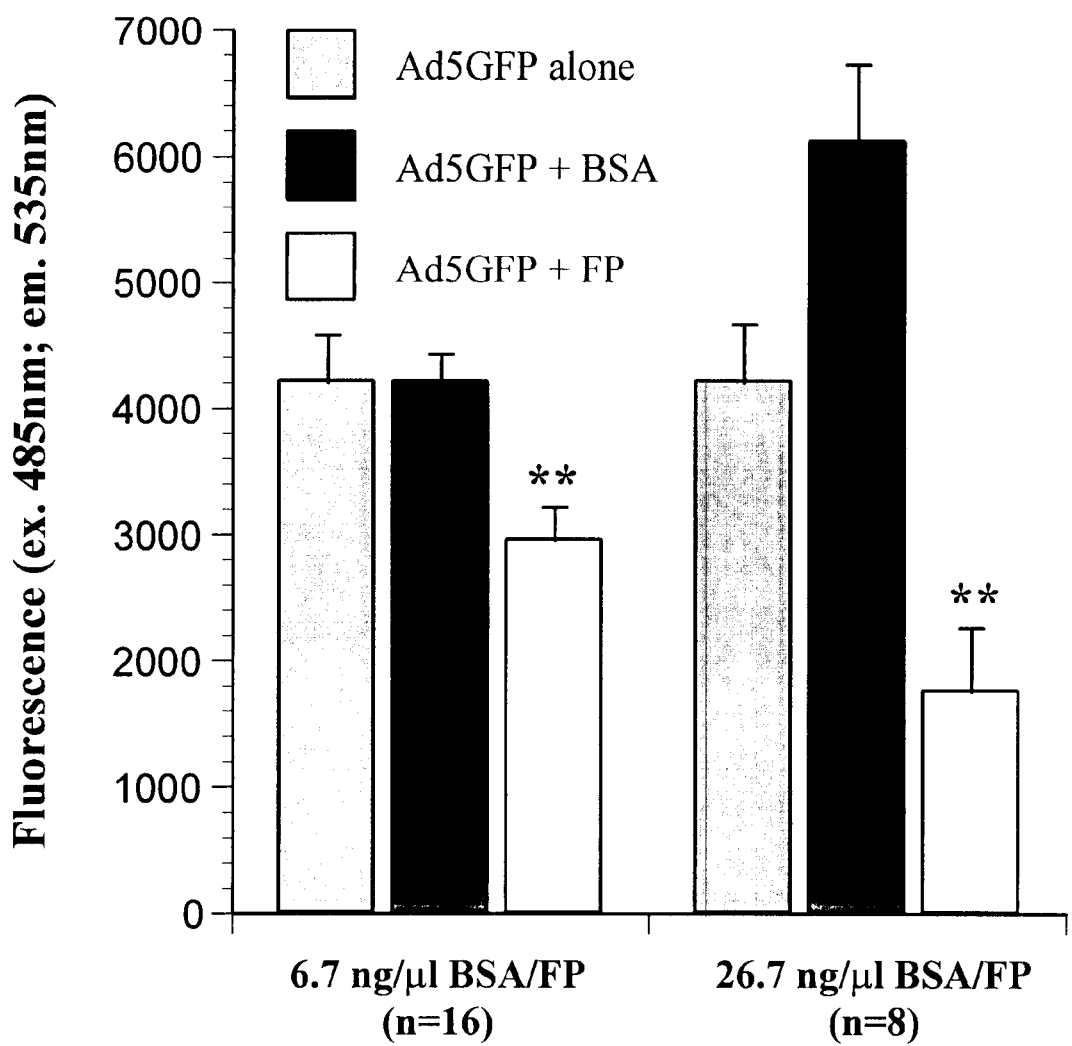
Figure 7:
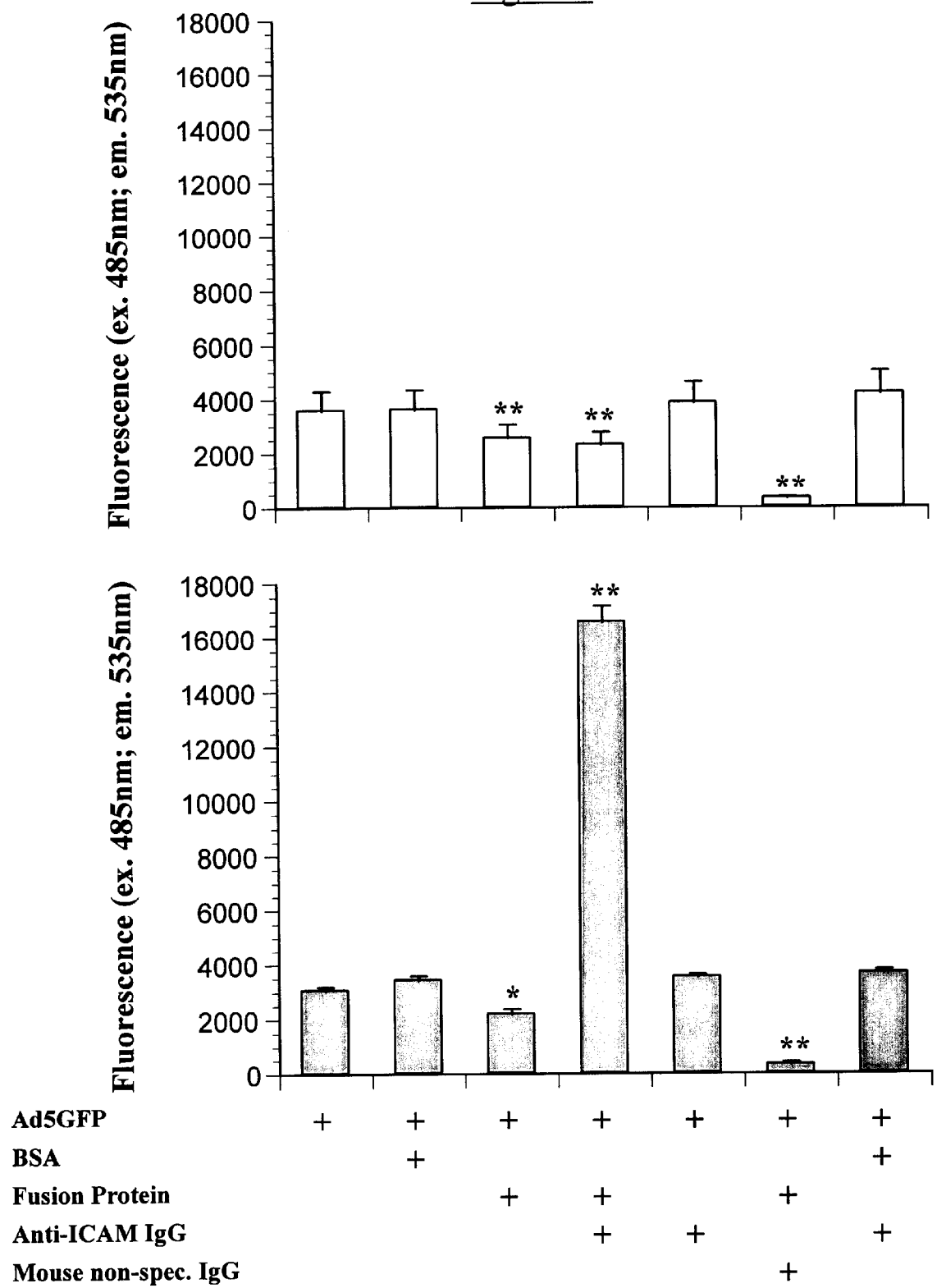
Figure 8:
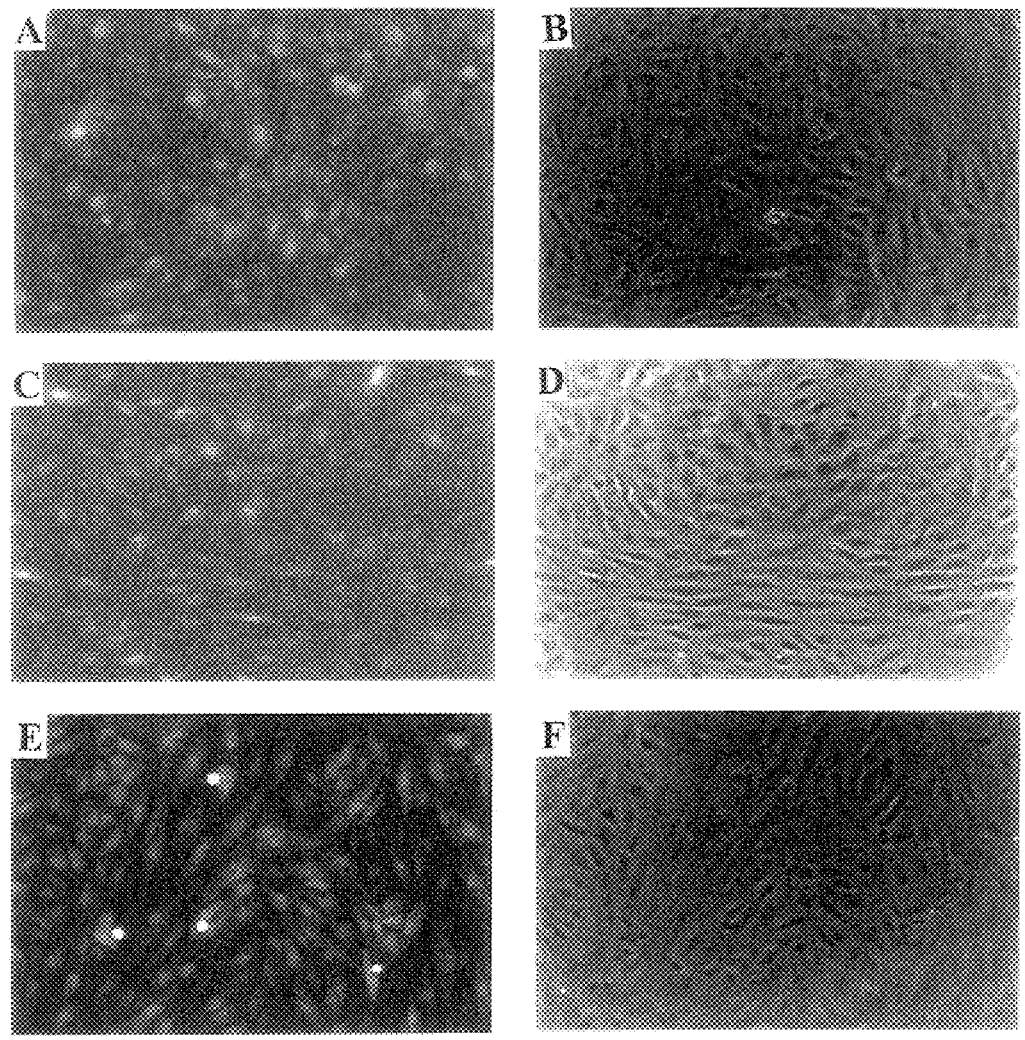

A large-scale culture from this colony was performed for harvesting purified fusion protein ligand. The fusion protein in the supernatant was purified using the Xpress Protein Purification System (purchased from Invitrogen) according to the manufacture's suggested protocol. Briefly, the fusion protein was eluted from a resin column with 0.5 M imidazole in phosphate buffer at 4° C. The eluted fractions containing fusion protein determined by Western analysis, in 12 ml total, were combined and dialyzed extensively against PBS at 4° C. This was followed by about 40-fold concentration with Centricon filters. The concentrated fusion protein was reconstituted in a storage solution (the storage buffer contains 50% glycerol, 12.5 µg/ml BSA, 1 mM DDT, 0.1 mM EDTA in 50 mM phosphate buffer, pH 7.4), and stored at −20° C. Protein concentration was determined using a BioRad (Hercules, Calif.) protein assay kit. Recovery of the CAR/Hg/Pro-A ligand was assessed by Western hybridization and the purity by Coomassie Blue staining. A band migrating at approximately 45 kD, corresponding to the estimated molecular weight of CAR/Hg/Pro-A ligand, was identified by both Western hybridization (Drawing 3C, lane 1) and Commassie Blue staining (lanes 2 and 3). We found that CAR/Hg/Pro-A was the major protein constituent in the crude culture medium before purification (lane 3 of Drawing 3C) and in the final purified storage form, it constituted at least 90% of total protein as judged by Coomassie straining (FIG. 3C, lane 2). Thus the yield of CAR/Hg/Pro-A from a 40-ml culture was about 0.4 mg (spec. protein conc. is 0.2 mg/ml).

II. Targeting recombinant adenovirus using CAR/Hg/Pro-A fusion protein ligand and anti ICAM-1 antibody to cultured TNF-α treated, ICAM-1 expressing human umbilical vascular endothelial cells (HUVEC):

1. Induction of ICAM-1 expression by TNF-α in cultured HUVEC:

HUVEC were purchased from Clonetics (San Diego, Calif.), and maintained at 37° C. in humidified air containing 5% $CO_2$ in growth medium (EGM-2) from Clonetics. Typically, HUVEC at passage of 5 or 6 were used for experiments and were seeded from T25 flasks to 96-well plates at approximately $2\times10^4$ cells per well. Confluent mature HUVEC assumed a flat spindle-like shape under microscopic examination. When cells reached confluence they were starved for 1-day in EBM-2 (a basic medium) to induce quiescence. The level of ICAM-1 expression was assessed using an immunoassay described by Zund et al (Zund, et al., 1996, Proc Natl Acad Sci USA 93, 7075–80.). Briefly, cells, at different time points after TNF-α treatment (0.1 µg/ml, Calbiochem, La Jolla, Calif.), were fixed in 1% paraformaldehyde followed by blocking with 1% BSA in PBS, and incubated with 5 µg/ml purified mouse monoclonal antibody against human ICAM-1 (PharMingen, San Diego, Calif.). After washing, cells were incubated with horseradish peroxidase (HRP)-conjugated rat anti mouse IgG and peroxidase substrate, 2,2'-azino-dis(3,ethylbenzthiazoline-6-sulphonic acid). The blue color developed was measured quantitatively at 405 nm with a plate spectrophotometer. The value at each time point was determined in quadruplicate wells. In agreement with reports in literature (Wojciak-Stothard, et al., 1999, J Cell Biol 145, 1293–307.), it was found that normal endothelial cells did not express ICAM-1 and the expression of ICAM-1 was significantly induced in cultured HUVEC after 4 hours of TNF-α treatment (Drawing 4). The level of ICAM-1 expression continued to climb up even at 48 hours after treatrnent. In this experiment we did not include time points longer than 48 hours after TNF-α treatment, therefore the peak ICAM-1 expression was not observed.

2. Titration of the transfection efficiency of Ad5GFP in cultured normal or TNF-α treated (24 hour) HUVEC:

Titration of viral transfection efficiency was performed in a 30-µl volume per well in starvation medium in the 96-well plate. The virus was added with serial 1:4 dilutions in the starvation medium. Cells with or without TNF-α treatment were incubated with virus containing starvation medium for one hour at 37° C. followed by washing and replacement with fresh starvation medium. To measure viral transfection efficiency quantitatively we used a recombinant adenovirus species that expresses green fluorescent protein, named Ad5GFP, and at 40 hours after Ad5GFP transfection the green fluorescence produced from Ad5GFP transfected cells was measured. Comparing with normal HUVEC, HUVEC after TNF-α treatment was found expressing a significantly lower level of GFP (Drawing 5). Although not proven from these data, it is suggested that TNF-α treated HUVEC are refractory to viral infections.

3. Inhibition of Ad5GFP-mediated gene transfection in HUVEC by CAR/Hg/Pro-A ligand:

The activity of CAR/Hg/Pro-A to inhibit Ad5GFP to transfect target cells was tested in both normal and TNF-α treated HUVEC. Ad5GFP at 43.8 MOI (MOI=viral titer/cell number) was used to infect normal HUVEC in the presence of CAR/Hg/Pro-A ligand (7.6 ng/µl or 26.7 ng/µl in viral containing starvation medium), and the transfection efficiency was reduced by 29% and 58%, respectively in the presence of CAR/Hg/Pro-A ligand (Drawing 6, **$\rho<0.01$). In the presence of BSA at the same protein concentration, there was no reduction of viral transfection efficiency. In TNF-α treated endothelial cells, the blocking effect was determined using different viral titer during transfection with the same concentration of fusion protein ligand (7.6 ng/µl in viral containing starvation medium). At higher viral titer (MIO=699), CAR/Hg/Pro-A ligand reduced the transfection efficiency by 19.5% ($\rho<0.05$) whereas at lower viral titer (MIO=175) CAR/Hg/Pro-A ligand reduced the transfection efficiency by 27.2% ($\rho<0.05$). Again, presence of BAS during transfection had no effect on transfection efficiency.

4. Re-targeting of Ad5GFP in ICAM-1 expressing HUVEC by fusion protein ligand, CAR/Hg/Pro-A, in complex with anti ICAM-1 IgG:

To demonstrate that CAR/Hg/Pro-A is capable of re-directing Ad5GFP when coupled with a specific antibody against cell surface marker, anti ICAM-1 IgG (CALTAG, Lab., Burlingame, Calif.) was preincubated with CAR/Hg/Pro-A and Ad5GFP before transfecting TNF-α treated HUVEC. HUVEC, at 24 hour after TNF-α treatment, were transfected with 699 MOI Ad5GFP that had been preincubated with CAR/Hg/Pro-A and antibody. As controls, normal HUVEC was also transfected. The Ad5GFP, CAR/Hg/Pro-A and anti ICAM-1 complex were allowed to form at room temperature for 1 hour before transfection. As expected, in the presence of anti ICAM-1 IgG and CAR/Hg/Pro-A ligand, Ad5GFP transfect TNF-α treated HUVEC at much high efficiency than all other controls (Drawing 7, bottom).

As controls, Ad5GFP alone, and Ad5GFP plus BSA were used to determine viral transfection efficiency. Ad5GFP plus CAR/Hg/Pro-A, or Ad5GFP plus CAR/Hg/Pro-A ligand and nonspecific mouse IgG were also used as controls to determine the specificity of targeting. In another control, Ad5GFP plus anti ICAM-1 IgG was used. This control is to demonstrate that only in combination of CAR/Hg/Pro-A and anti ICAM- 1 IgG will the viral transfection efficiency by Ad5GFP be increased. Non-specific IgG in replacement of anti ICAM-1 IgG will not have this effect. Because normal endothelial cells do not express ICAM-1, as anticipated, complexation of Ad5GFP with CAR/Hg/Pro-A ligand and anti ICAM-1 IgG did not increased the viral transfection efficiency in normal HUVEC (Drawing 7, top). Of note, the increased viral transfection efficiency with Ad5GFP, CAR/Hg/Pro-A ligand and anti ICAM-1 IgG complex in TNF-α treated HUVEC suggests that reduced green fluorescence in TNF-α treated cells by Ad5GFP, seen in Drawing 5, is likely to be the result of reduced efficiency in viral transfection rather than other processes that may inhibit GFP expression.

III. Targeting recombinant adenovirus to human CD34$^+$ bone marrow stem cells:

Human hematopoietic stem cells (HSC) are important target for gene therapy. Most of HSC are in a quiescent state and refractory for gene transfection by retroviral based gene delivery system that requires targeting cells in proliferating stage. Most of HSC express CD34$^+$ as marker and CD34$^+$ is also internalized efficiently through cell endocytosis pathway (Fackler, et al., 1992, J Biol Chem 267, 17540–6.). Because of low level of CAR expression CD34$^+$ hematopoietic progenitor cells are refractory for adenovirus based gene transfection (Shayakhmetov, et al., 2000, J Virol 74, 2567–83.). This precludes the direct use of adenovirus based gene delivery system for gene therapy in CD34$^+$ stem cells. However, current invention overcomes this limitation. With CAR/Hg/Pro-A and anti CD34 IgG, the transfection efficiency in CD34$^+$ hematopoietic progenitor cells by adenovirus can be increased. It also increases the selectivity and improves the safety for use adenovirus based gene delivery system in these cells.

1. Harvest and culture of human CD34$^+$ hematopoietic stem cells:

Human CD34$^+$ enriched bone marrow cells are purified from bone marrow or peripheral blood using Direct CD34 Progenitor Cell Isolation Kit with MACS VS$^+$ separation columns (purchased from Miltenyi Biotec, Auburn, Calif.) according to the manufacturer's instructions. The Direct CD34 Progenitor Cell Isolation Kit contains MicroBeads conjugated to CD34 antibodies for magnetic labeling of CD34 expressing hematopoietic progenitor cells from bone marrow or peripheral blood. CD34$^+$ hematopoietic progenitor cells can be magnetically labeled using MACS CD34 MicroBeads. Hematopoietic progenitor cells, present at a frequency of about 0.05–0.2% in peripheral blood and 0.5–3% in bone marrow, can be rapidly and efficiently enriched to a purity of about 85–98%.

Briefly, to harvest from peripheral blood, fresh human blood treated with an anticoagulant are diluted with 2–4 volumes of PBS containing 2 mM EDTA. To harvest from bone marrow, bone marrow is placed in 50-ml tubes containing 5 ml PBS containing 2 mM EDTA. For release of the cells, above mixture is diluted in 10×excess of RPMI 1640 containing 0.02% collagenase B and 100 U/ml DNAse and shake gently at room temperature for 45 minutes. Pass cells through 30-μm nylon mesh. Following steps is the same for both cells from peripheral blood or bone marrow. Carefully place 35 ml of diluted cell suspension either from peripheral blood or from bone marrow over 15 ml of Ficoll-Paque® (1.077 density, purchased Sigma, St. Louis, Mo.) in a 50 ml conical tube and centrifuge at 400×g for 30–40 minutes at 20° C. in a swinging-bucket rotor without brake. Aspirate the upper layer leaving the mononuclear cell layer undisturbed at the interphase. Carefully transfer the interphase cells (lymphocytes and monocytes) to a new 50-ml conical tube. Fill the conical tube with PBS containing 2 mM EDTA, mix and centrifuge at 300×g for 10 minutes at 20° C. Carefully remove the supernatant completely. Wash the cell pellet once more with PBS containing 2 mM EDTA and carefully remove the supernatant completely after centrifugation. Resuspend cell pellet in a final volume of 300 μl per $10^8$ total cells.

Add 100 μl FcR Blocking Reagent per $10^8$ total cells to the cell suspension to inhibit unspecific or Fc-receptor mediated binding of CD34 MicroBeads to non-target cells. Label cells by adding 100 μl CD34 MicroBeads per 108 total cells, mix well and incubate for 30 minutes at 6°–12° C. Wash cells carefully and resuspend in 1–10 ml of buffer.

Insert VS+ Column Adapter in the magnetic field of VarioMACS. Place the VS+Separation Column in the VS+Column Adapter. Apply 3 ml of degassed PBS supplemented with 2 mM EDTA and 0.5% BSA on top of the column and let the buffer run through. Apply cells to the column, allow cells to pass through the column and wash column with 4×3 ml buffer and discard effluent. Remove column from separator and place on the holder. Apply 5 ml of buffer to the reservoir of the VS+column and flush out cells using the plunger supplied with the column. Aliquots of harvested cells are stored in liquid nitrogen.

Sixteen hours before the experiment, cells are recovered from the frozen stock and incubated in growth medium at 37° C. The growth medium contains Iscove modified Dulbecco medium supplemented with 20% FCS, $10^{-4}$ M β-mercaptoethanol, 100 μg of DNase I per ml, 2 mM glutamine, 10 U of interieukin-3, and 50 ng of stem cell factor (SCF) or 2 ng of thrombopoietin per ml. The purity of CD34$^+$ preparations can be verified by flow cytometry.

2. Determination of transfection efficiency of human CD34$^+$ hematopoietic stem cells with Ad5GFP:

CD34$^+$ stem cells at $10^5$ to $10^7$ cells/ml in 30 to 50 μl are infected with Ad5GFP at various MIO at 37° C. for one to two hours. After incubation, the cells are centrifuged at 1,000×g for 5 min, the virus containing medium is removed, and the cells are resuspended in 100 μl of fresh medium and then incubated at 37° C. until harvesting. Thirty-six to forty-eight hours after transfection cells are collected by centrifugation and washed once with PBS. After resuspended in fresh PBS, transfection efficiency is determined by measuring green fluorescence produced from GFP in Ad5GFP transfected cells in PBS in the wells as performed with endothelial cell cultures.

3. Determination of blocking efficiency of CAR/Hg/Pro-A in Ad5GFP mediated viral gene transfection:

As experiments performed in HUVEC, gradual increase of the viral titer (MIO) correspondingly increases viral gene transfection. In CD34$^+$ stem cells, there also is a dose range in which increase of viral titer correlates linearly increase of viral gene transfection. The viral titer in this dose range will be used in subsequent experiments to determine the blocking efficiency with various dose of CAR/Hg/Pro-A ligand. Blocking experiments are performed by gradual increase of CAR/Hg/Pro-A concentration with a fixed MIO of Ad5GFP during preincubation period. CD34$^+$ stem cells are centrifuged to remove culture medium and are incubated with medium containing virus and ligand protein at 37° C. for one hour. Thirty-six to forty-eight hours after transfection cells are collected by centrifugation and washed once with PBS. After resuspended in fresh PBS, transfection efficiency is determined by measuring green fluorescence produced from GFP in Ad5GFP transfected cells in PBS in the wells. The result of these experiments determines the doses of CAR/Hg/Pro-A required to completely or near-completely block the viral transfection in CD34$^+$ cells.

4. Redirecting Ad5GFP to human CD4$^+$ hematopoietic stem cells with fusion protein ligand and anti CD34 IgG:

Once viral titer (MIO) and blocking dose of CAR/Hg/Pro-A is determined, at determined viral titer and blocking dose, anti-CD34 antibody (obtained from Becton Dickinson Immuno-cytochemistry Systems, San Jose, Calif., or many other sources), and CAR/Hg/Pro-A ligand protein is added together in preincubation medium with the Ad5GFP. After preincubation, the viral containing medium is used to transfect CD34$^+$ cells selectively under the same experimental condition and detection method. With the use of Ad5GFP, CAR/Hg/Pro-A and anti CD34 IgG complex, the transfection efficiency by recombinant adenovirus is increased and the length of transgene expression in these cells are increased as well.

I claim:

1. A method of targeting viral entry into cells, comprising combining a fusion protein ligand comprising an antibody binding region and a viral receptor, wherein the viral receptor binds to a viral vector, with an antibody which has a region recognized by said antibody binding region and which binds to a target cell surface molecule, and further with a viral vector comprising a recombinant nucleic acid encoding a heterologous therapeutic protein and a viral surface molecule bound by said receptor wherein the fusion protein ligand-viral receptor-antibody complex targets said viral vector to a cell wherein viral entry occurs.

2. The fusion protein ligand of claim 1 further comprising a) a viral receptor, wherein the viral receptor is linked to b) a linker amino acid polypeptide, wherein one end of the linker polypeptide is linked to the viral receptor, and the other end of the linker polypeptide is linked to c) an antibody binding protein.

3. The fusion protein ligand of claim 2, wherein the viral receptor portion is a soluble, extracellular portion of a viral receptor.

4. The fusion protein ligand of claim 2, wherein the linker amino acid polypeptide portion is a linker polypeptide wherein one end of the linker covalently links to the viral receptor and the other end links covalently to the antibody binding protein.

5. The fusion protein ligand of claim 2, wherein the antibody binding protein portion is a soluble protein which binds to an antibody.

6. The viral vector of claim 1 wherein the therapeutic protein, which is encoded from a recombinant nucleic acid sequence in the viral genome of said viral vector, is selected by the group consisting of: immunogenes cytokines, tumor necrosis factor, interferons, interleukins, adenosine daminase, insulin, T-cell receptors, soluble CD4, epidermal growth factor, human growth factor, blood factors, such as Factor VIII, Factor IX, cytochrome b, glucocerebrosidase, ApoE, ApoC, ApoA1, the LDL receptor, negative selection markers, anti-angiogenic factors, Fc receptors, plasminogen activators, dopamine, MHC, tumor suppressor genes, monoclonal antibodies or antigen binding fragments thereof, drug resistance genes, ion channels, adrenergic receptors, an intracellular protein which is a component transducing intracellular signals, a component cellular apoptosis protein, or a component to inhibit signal transduction and a protein that inhibits cellular apoptotic processes.

7. The fusion protein ligand of claim 3, wherein the viral receptor portion is a soluble, extracellular portion of an adenoviral vector.

8. The fusion protein ligand of claim 7, wherein the viral receptor portion is a soluble, extracellular portion of the coxsackievirus/adenovirus receptor, CAR.

9. The fusion protein ligand of claim 4, wherein the linker amino acid polypeptide portion is a hinge region from a mouse immunoglobulin polypeptide wherein one end covalently links to the viral receptor and the other end links covalently to the antibody binding protein.

10. The fusion protein ligand of claim 5, wherein the antibody binding protein portion is a soluble protein which binds specifically to the Fc region of an antibody.

11. The fusion protein ligand of claim 10, wherein the antibody binding protein portion is a soluble antibody Fc binding domain from Protein A.

12. The fusion protein ligand CAR/Hg/Pro-A, having its amino acid sequence given in Drawing 3B in Bald.

* * * * *

SEQUENCE LISTING

<160> NUMBER OF SEQ ID NOS: 8

<210> SEQ ID NO 1
<211> LENGTH: 23
<212> TYPE: DNA
<213> ORGANISM: Homo sapiens origin with alteration to generate an EcoRI
      site

<400> SEQUENCE: 1
gtggaattcg ccagaagttt gag                                             23

<210> SEQ ID NO 2
<211> LENGTH: 22
<212> TYPE: DNA
<213> ORGANISM: Homo sapiens origin with alteration to generate a NotI
      site

<400> SEQUENCE: 2
taatggcggc cgcaattagt cc                                              22

<210> SEQ ID NO 3
<211> LENGTH: 22
<212> TYPE: DNA
<213> ORGANISM: staphylococcus aureus origin with alteration to generate
      a NotI site

<400> SEQUENCE: 3
cgatgcggcc gcagacaaca aa                                              22

<210> SEQ ID NO 4
<211> LENGTH: 21
<212> TYPE: DNA
<213> ORGANISM: staphylococcus aureus origin with alteration to generate
      an XbaI site

<400> SEQUENCE: 4
gcgtctgatt cggcgcctga g                                               21

<210> SEQ ID NO 5
<211> LENGTH: 36
<212> TYPE: DNA
<213> ORGANISM: mus origin with alteration to generate a partial NotI
      site

<400> SEQUENCE: 5
ggccccgaaa cgagcacccc gccggggcag cagcgc         36

<210> SEQ ID NO 6
<211> LENGTH: 36
<212> TYPE: DNA
<213> ORGANISM: mus origin with alteration to generate a partial NotI
      site

<400> SEQUENCE: 6
ggccgcgctg ctgcccggcg gggtcgacgg tttcgg         36

<210> SEQ ID NO 7
<211> LENGTH: 1401
<212> TYPE: DNA
<213> ORGANISM: Homo sapiens, mus and staphylococcus aureus

<400> SEQUENCE: 7
atgagatttc cttcaattttt tactgctgtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc cattttccaa cagcacaaat     180
aacgggttat tgtttataaa tactactatt gccagcattg ctgctaaaga agaagggta     240
tctctcgaga aaagagaggc tgaagctgaa ttcgccagaa gtttgagtat cactactcct     300
gaagagatga ttgaaaaagc caagggggaa actgcctatc tgccgtgcaa atttacgctt     360
agtcccgaag accagggacc gctggacatc gagtggctga tatcaccagc tgataatcag     420
aaggtggatc aagtgattat tttatattct ggagacaaaa tttatgatga ctactatcca     480
gatctgaaag gccgagtaca ttttacgagt aatgatctca atctggtga tgcatcaata     540
aatgtaacga atttacaact gtcagatatt ggcacatatc agtgcaaagt gaaaaaagct     600
cctggtgttg caaataagaa gattcatctg gtagttcttg ttaagccttc aggtgcgaga     660
tgttacgttt atggatctga agaaattgga agtgactttta agataaaatg tgaaccaaaa     720
gaaggttcac ttccattaca gtatgagtgg caaaaattgt ctgactcaca gaaaatgccc     780
acttcatggt tagcagaaat gacttcatct gttatatctg taaaaaatgc ctcttctgag     840
tactctggga catacagctg tacagtcaga acagagtgg gctctgatca gtgcctgttg     900
cgtctaaacg ttgtccctcc ttcaaataaa gctggactaa ttgcggcccc gaaaccgtcg     960
accccgccgg gcagcagcgc ggccgcagac aacaaattca caaagaaca caaaacgcg    1020
ttctatgaga tcttacatttt acctaactta acgaagaac aacgaaacgc cttcatccaa    1080
agtttaaaag atgacccaag ccaaagcgct aaccttttag cagaagctaa aaagctaaat    1140
gatgctcagg cgccgaaagt agacaacaaa ttcaacaaag aacaacaaaa cgcgttctat    1200
gagatcttac atttacctaa cttaaacgaa gaacaacgaa acgccttcat ccaaagttta    1260
aaagatgacc caagccaaag cgctaaccttt tagcagaag ctaaaaagct aaatgatgct    1320
caggcgccga atctagaaca aaaactcatc tcagaagagg atctgaatag cgccgtcgac    1380
catcatcatc atcatcattg a                                               1401

<210> SEQ ID NO 8
<211> LENGTH: 466
<212> TYPE: PRT
<213> ORGANISM: Homo sapiens, mus and staphylococcus aureus

<400> SEQUENCE: 8

-continued

```
Met Arg Phe Pro Ser Ile Phe Thr Ala Val Leu Phe Ala Ala Ser Ser
 1               5                  10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
                35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe Ala Arg Ser Leu Ser
                85                  90                  95

Ile Thr Thr Pro Glu Glu Met Ile Glu Lys Ala Lys Gly Glu Thr Ala
                100                 105                 110

Tyr Leu Pro Cys Lys Phe Thr Leu Ser Pro Glu Asp Gln Gly Pro Leu
                115                 120                 125

Asp Ile Glu Trp Leu Ile Ser Pro Ala Asp Asn Gln Lys Val Asp Gln
    130                 135                 140

Val Ile Ile Leu Tyr Ser Gly Asp Lys Ile Tyr Asp Asp Tyr Tyr Pro
145                 150                 155                 160

Asp Leu Lys Gly Arg Val His Phe Thr Ser Asn Asp Leu Lys Ser Gly
                165                 170                 175

Asp Ala Ser Ile Asn Val Thr Asn Leu Gln Leu Ser Asp Ile Gly Thr
                180                 185                 190

Tyr Gln Cys Lys Val Lys Lys Ala Pro Gly Val Ala Asn Lys Lys Ile
                195                 200                 205

His Leu Val Val Leu Val Lys Pro Ser Gly Ala Arg Cys Tyr Val Asp
    210                 215                 220

Gly Ser Glu Glu Ile Gly Ser Asp Phe Lys Ile Lys Cys Glu Pro Lys
225                 230                 235                 240

Glu Gly Ser Leu Pro Leu Gln Tyr Glu Trp Gln Lys Leu Ser Asp Ser
                245                 250                 255

Gln Lys Met Pro Thr Ser Trp Leu Ala Glu Met Thr Ser Ser Val Ile
                260                 265                 270

Ser Val Lys Asn Ala Ser Ser Glu Tyr Ser Gly Thr Tyr Ser Cys Thr
    275                 280                 285

Val Arg Asn Arg Val Gly Ser Asp Gln Cys Leu Leu Arg Leu Asn Val
    290                 295                 300

Val Pro Pro Ser Asn Lys Ala Gly Leu Ile Ala Ala Pro Lys Pro Ser
305                 310                 315                 320

Thr Pro Pro Gly Ser Ser Ala Ala Asp Asn Lys Phe Asn Lys Glu
                325                 330                 335

Gln Gln Asn Ala Phe Tyr Glu Ile Leu His Leu Pro Asn Leu Asn Glu
                340                 345                 350

Glu Gln Arg Asn Ala Phe Ile Gln Ser Leu Lys Asp Asp Pro Ser Gln
                355                 360                 365

Ser Ala Asn Leu Leu Ala Glu Ala Lys Lys Leu Asn Asp Ala Gln Ala
    370                 375                 380

Pro Lys Val Asp Asn Lys Phe Asn Lys Glu Gln Gln Asn Ala Phe Tyr
385                 390                 395                 400

Glu Ile Leu His Leu Pro Asn Leu Asn Glu Glu Gln Arg Asn Ala Phe
                405                 410                 415
```

-continued

```
Ile Gln Ser Leu Lys Asp Asp Pro Ser Gln Ser Ala Asn Leu Leu Ala
            420                 425                 430

Glu Ala Lys Lys Leu Asn Asp Ala Gln Ala Pro Asn Leu Glu Gln Lys
        435                 440                 445

Leu Ile Ser Glu Glu Asp Leu Asn Ser Ala Val Asp His His His His
    450                 455                 460

His His
465
```